United States Patent
Modglin et al.

(10) Patent No.: US 10,143,582 B2
(45) Date of Patent: Dec. 4, 2018

(54) ADJUSTABLE BACK BRACE

(71) Applicant: DeRoyal Industries, Inc., Powell, TN (US)

(72) Inventors: Michael D. Modglin, Braselton, GA (US); Kathleen L. Parker, Knoxville, TN (US); Charles J. French, III, Knoxville, TN (US); Tyson A. R. White, Andersonville, TN (US)

(73) Assignee: DeRoyal Industries, Inc., Powell, TN (US)

(*) Notice: Subject to any disclaimer, the term of this patent is extended or adjusted under 35 U.S.C. 154(b) by 333 days.

(21) Appl. No.: 14/950,255

(22) Filed: Nov. 24, 2015

(65) Prior Publication Data

US 2016/0228279 A1 Aug. 11, 2016

Related U.S. Application Data

(60) Provisional application No. 62/114,345, filed on Feb. 10, 2015.

(51) Int. Cl.
*A61F 5/02* (2006.01)

(52) U.S. Cl.
CPC .................. *A61F 5/028* (2013.01)

(58) Field of Classification Search
CPC .. A61F 5/34; A61F 5/024; A61F 5/028; A61F 5/055; A61F 5/05883; A61F 5/026
See application file for complete search history.

(56) References Cited

U.S. PATENT DOCUMENTS

| 2,163,107 | A | | 6/1939 | Shatto et al. |
| 2,181,689 | A | * | 11/1939 | Bell ................... A61F 5/028 2/44 |
| 5,105,806 | A | | 4/1992 | Woodhouse et al. |
| 5,674,187 | A | * | 10/1997 | Zepf .................. A61F 5/024 24/578.15 |
| 6,500,137 | B1 | | 12/2002 | Molino et al. |
| 7,001,348 | B2 | | 2/2006 | Garth et al. |
| 8,142,377 | B2 | | 3/2012 | Garth et al. |
| 8,303,528 | B2 | | 11/2012 | Ingimundarson et al. |
| 8,435,196 | B2 | | 5/2013 | Bannister |
| 2010/0268141 | A1 | | 10/2010 | Bannister |
| 2010/0318011 | A1 | | 12/2010 | Hirota et al. |
| 2012/0253251 | A1 | | 10/2012 | Thornton |

(Continued)

FOREIGN PATENT DOCUMENTS

| EP | 0027602 A2 * | 4/1981 | ............. A61F 5/028 |
| WO | 2008142331 A2 | 11/2008 | |

OTHER PUBLICATIONS

WIPO International Searching Authority; PCT/US16/12125 International Search Report and Written Opinion dated Mar. 30, 2016; 9 pages.

*Primary Examiner* — Ophelia A Hawthorne
(74) *Attorney, Agent, or Firm* — Luedeka Neely Group, PC

(57) ABSTRACT

An adjustable length spinal brace includes an elongate belt and an adjustment plate having spaced apart belt passage slits through which the belt is passed and belt engagement members that are pivotally adjustable relative to the plate to engage or disengage the belt. The belt engagement members are engaged with the belt to maintain a desired length of the brace, and are disengaged from the belt to permit adjustment of the length of the brace.

5 Claims, 8 Drawing Sheets

(56) References Cited

U.S. PATENT DOCUMENTS

2013/0261522 A1* 10/2013 Billings .................. A61F 5/028
                                                        602/19
2013/0261523 A1    10/2013 Johnson
2014/0283284 A1     9/2014 Khorsandi

* cited by examiner

ADJUSTABLE BACK BRACE

CROSS REFERENCE TO RELATED APPLICATION

This application claims priority to U.S. Provisional Application 62/114,345, filed Feb. 10, 2015, entitled Adjustable Back Brace, and incorporated by reference herein in its entirety.

FIELD

This disclosure relates to the field of orthopedic bracing. More particularly, this disclosure relates to adjustable circumferential length lumbar sacral braces.

BACKGROUND

Improvement is desired in the provision of soft and flexible braces for supporting the thoraco-lumbro-sacral spine. While conventional lumbar belt type braces provide support, improvement is desired.

The present disclosure advantageously provides a soft and flexible lumbo-sacral brace to which can be added desired rigidity in an anterior, posterior and lateral portion of the belt adjacent the spine, and which is adjustable to fit a wide range of waist sizes circumferentially. One benefit of the flexibility of this brace design is a reduction of a large inventory of various sizes.

SUMMARY

The above and other needs are met by an adjustable circumferential length spinal brace. The brace includes an elongate belt and a belt adjustment plate.

The belt adjustment plate has an outer side and an opposite patient faceable side configured to be positionable adjacent a spine or back portion of a patient. The belt adjustment plate has spaced apart belt passage slits through which the belt is received and belt engagement members that are pivotally adjustable relative to the plate to engage or disengage the belt.

The belt engagement members are engaged with the belt to maintain a desired length of the brace, and are disengaged from the belt to permit adjustment of the length of the brace.

Braces according to the disclosure are advantageous as compared to prior devices. For example, the brace length may be easily and uniformly reduced or increased in length from a central location. This is accomplished by disengaging the belt engagement members, pulling a central portion of the belt to uniformly reduce the overall length, or pulling on each end to increase the length, and then engaging the belt engagement members.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
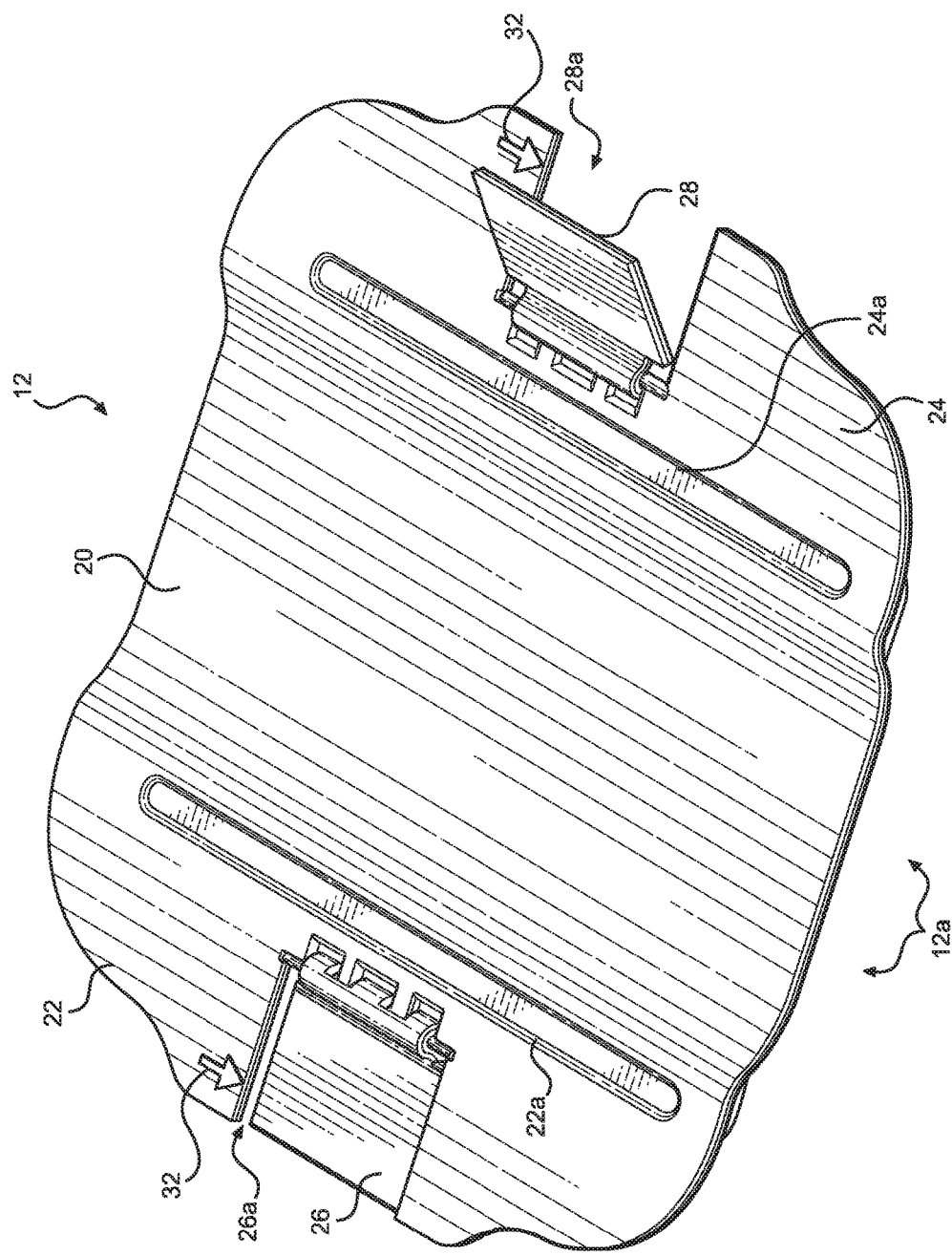
FIGS. 1 and 2 show an adjustment plate component of an adjustable brace according to the disclosure.
Figure 2:
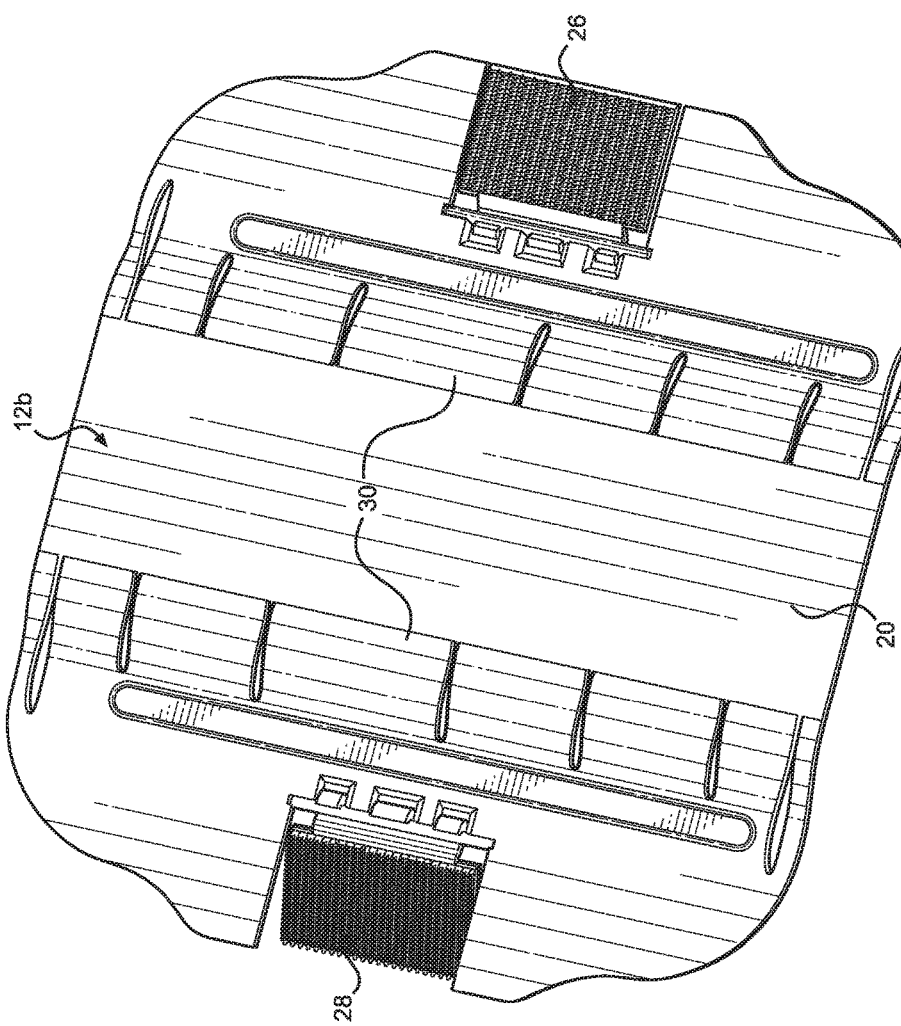
Figure 3:
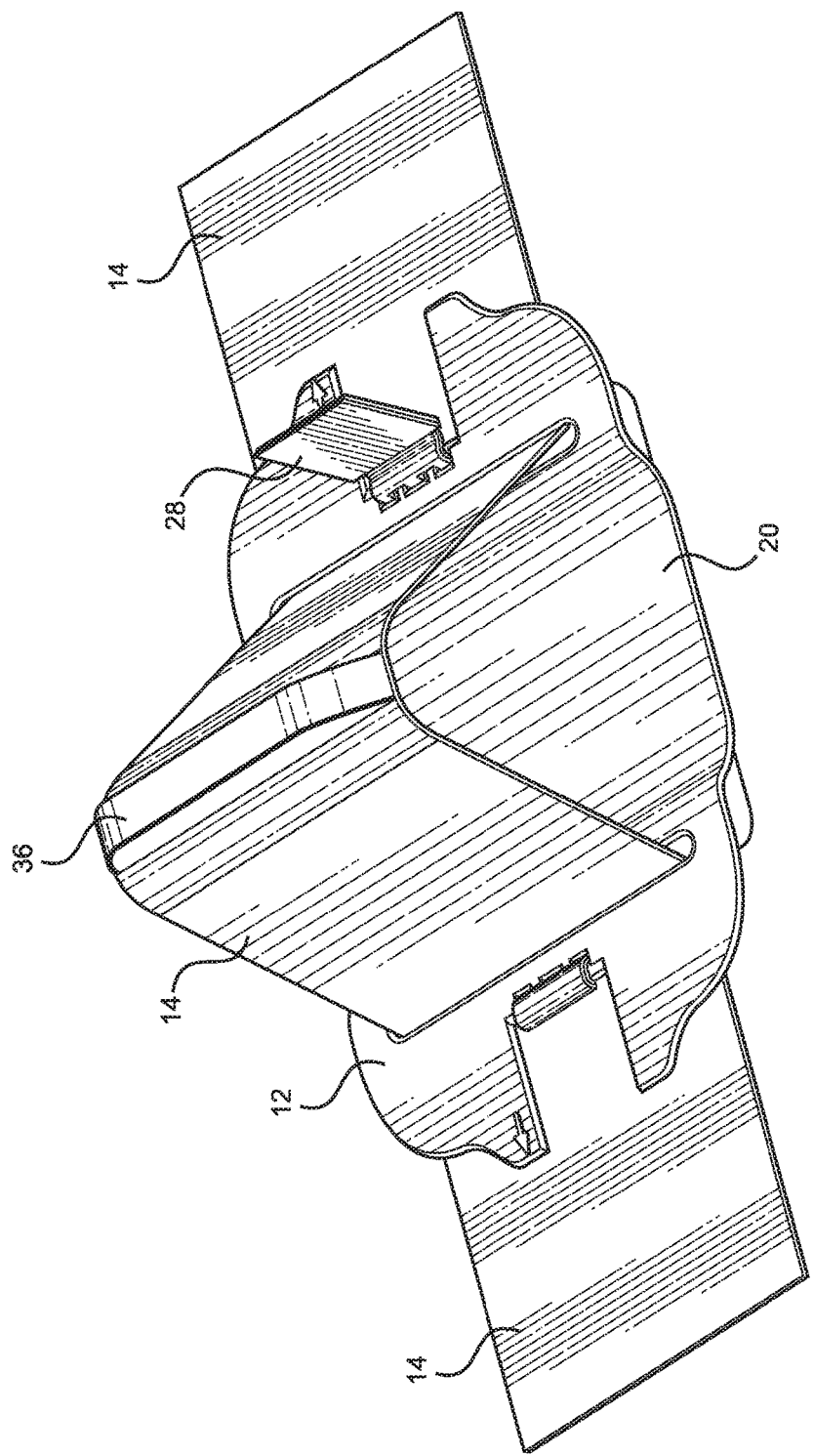
FIGS. 3 and 4 are front and rear views showing a belt component installed on the adjustment plate component.
Figure 4:
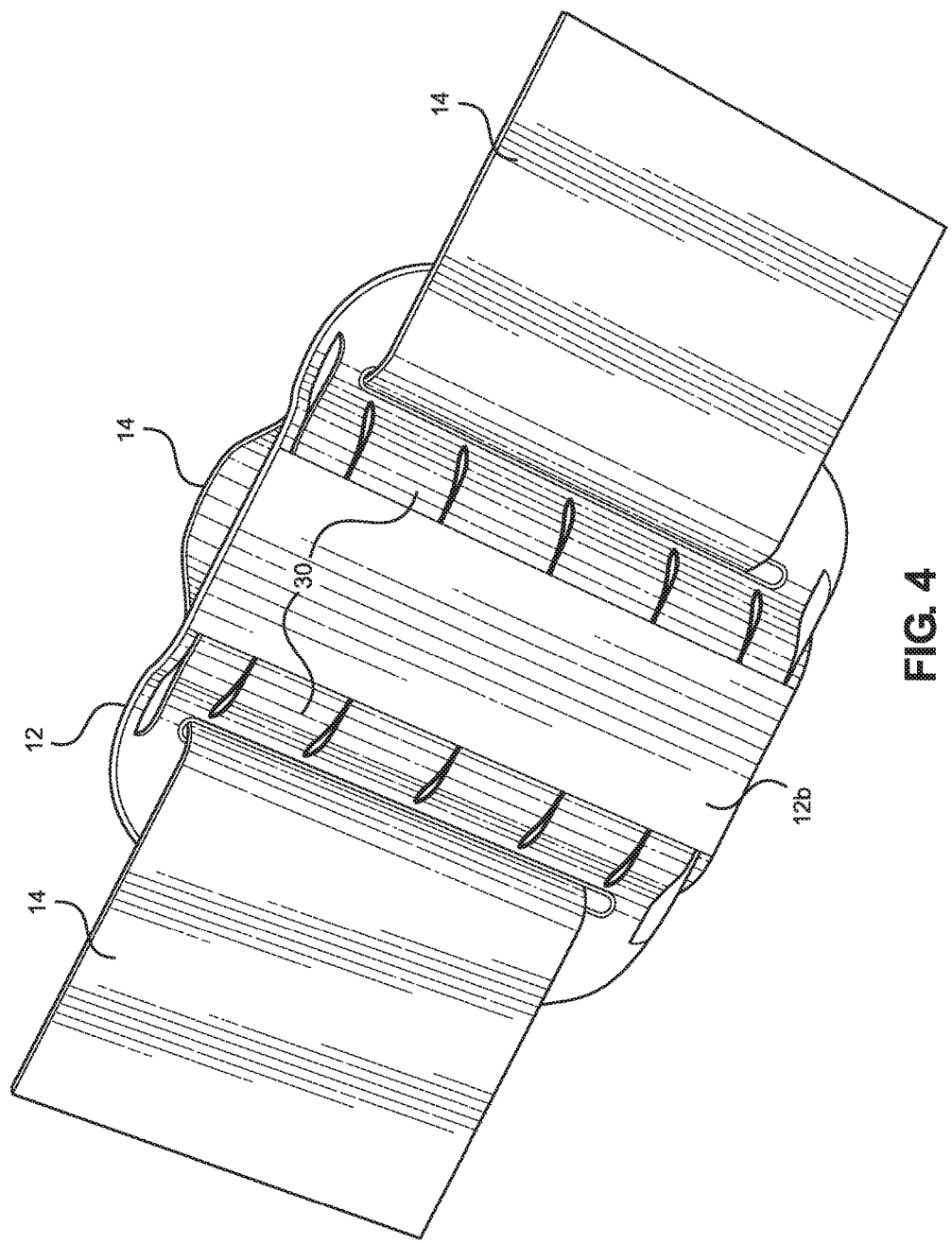
Figure 5:
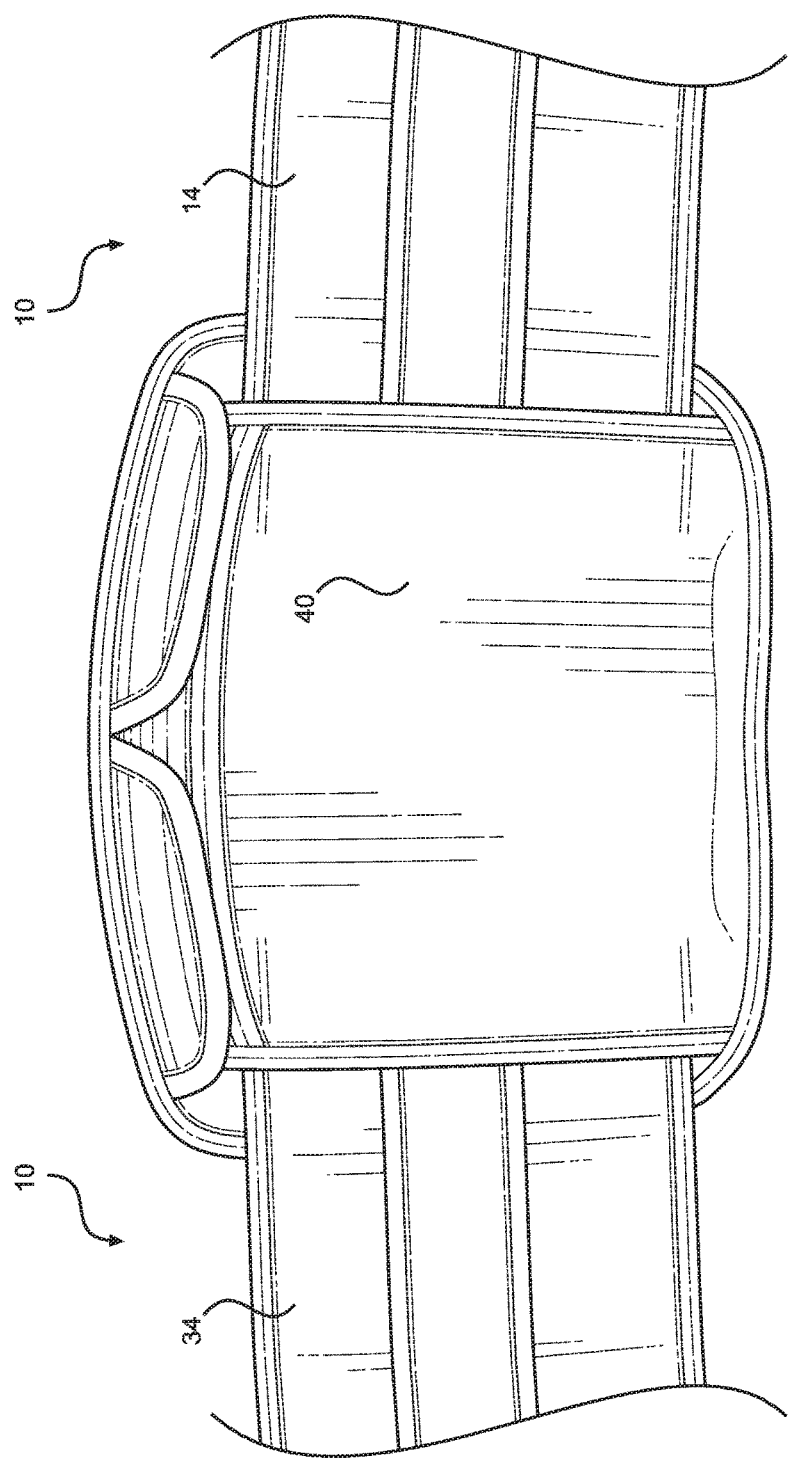
FIG. 5 shows an assembled adjustable brace according to the disclosure.
Figure 6:
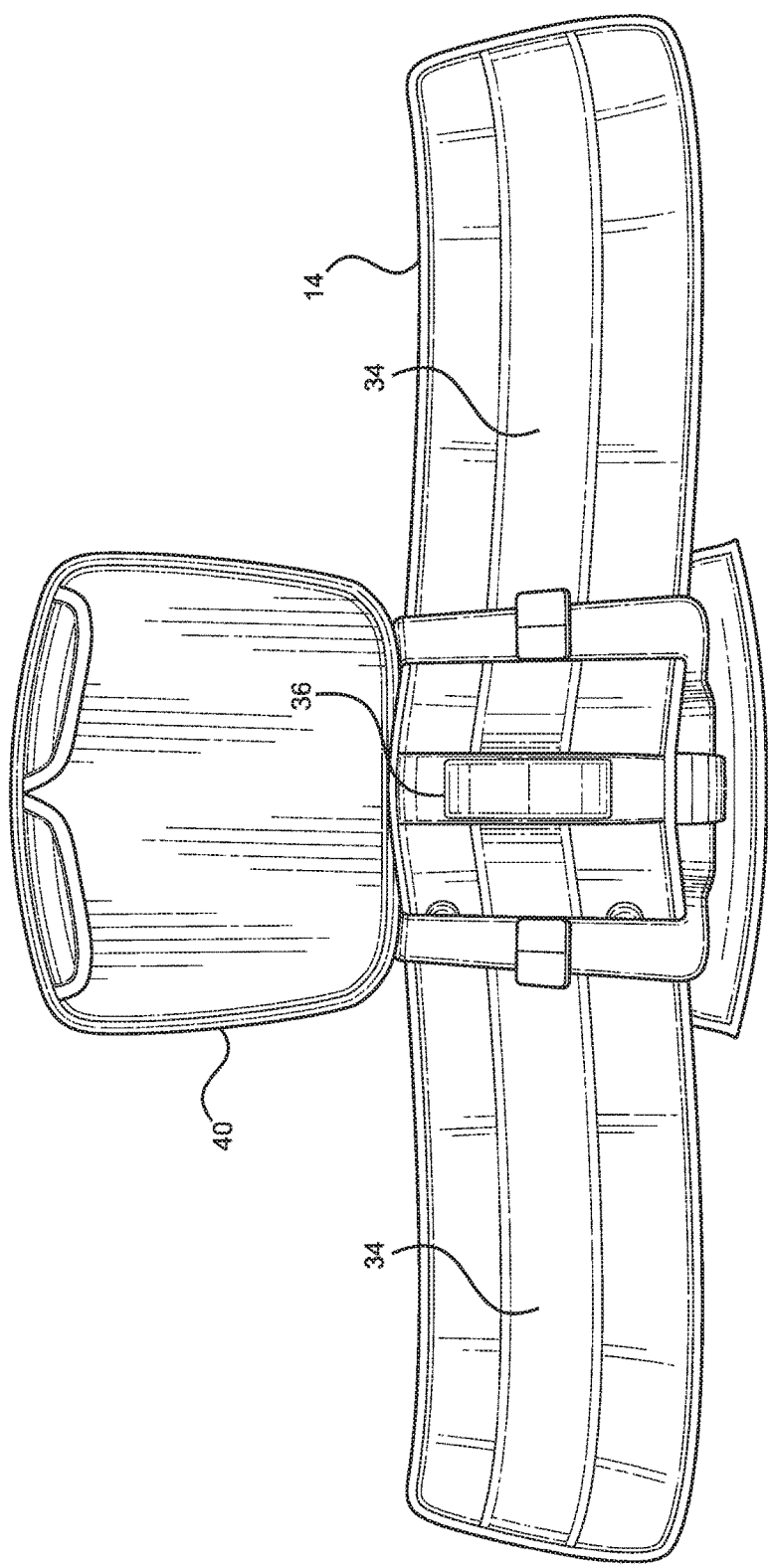
FIG. 6 shows the brace of FIG. 5 with a cover thereof opened with the brace set at a large size setting.

With reference to the drawings, there is shown an adjustable length lumbar sacral brace 10. The brace 10 includes an adjustment plate 12 and a belt 14.

The adjustment plate 12 is configured to be located adjacent the small of the back of a patient, and permit adjustment of the effective length of the belt 14. That is, the effective length of the belt 14 is adjusted utilizing the adjustment plate 12 so that the brace 10 desirably fits the waist of the patient.

The adjustment plate 12 may be of molded plastic construction and includes an outer side 12a and a patient facing side 12b. The plate 12 includes a mildly u-shaped or curved central channel portion 20 flanked on either side by planar portions 22 and 24. The curvature of the channel portion 20 is towards the patient facing side 12b. Belt passage slits 22a and 24a are located on the planar portions 22 and 24, respectively, adjacent the channel portion 20. Hinged belt engagement members 26 and 28 are defined adjacent the lateral edges of the planar portions 22 and 24, respectively.

The belt engagement members 26 and 28 are provided as doors that pivot relative to open spaces 26a and 28a, respectively, of the planar portions 22 and 24. The engagement members 26 and 28 pivot to open towards the outer side 12a of the plate 12. The patient facing side 12b of the engagement members 26 and 28 include a hook material thereon for releasably engaging a loop material of the belt 14, as explained more fully below. The patient facing side 12b of the adjustment plate 12 is positioned during use of the brace 10 adjacent the small of the back of the patient.

Flexible fingers 30 are located on the back of the channel portion 20 to provide a comfortable interface between the small of the back of the patient and the patient facing side 12b of the plate 12. The fingers 30 are preferably adjacent the slits 22a and 24a and extend the height of the plate 12. Size indicator indicia 32 is located on the outer side 12a for cooperating with size indicating zones of the belt 14, as explained more fully below.

The belt 14 is an elongate and flexible member preferably made of a soft fabric surrounding a batting or padding, such as a soft foam or spacer fabric. The belt 14 has opposite ends that releasably overlap or otherwise cooperate to install the belt about the waist of a user. To provide the brace 10 to adjust between waist sizes of from about 26 inches to about 44 inches, the belt 14 may have an overall length of about 48 inches.

The belt 14 preferably includes indicia or indicium, such as length demarcations or color zones or the like, that cooperate with the size indicator indicia 32 of the plate 12, to facilitate selection of desired size of the brace 10. The exterior of the belt 14 may be made of a loop material or a strip of loop material 34 may be located on the exterior surface of the belt 14 to cooperate with the hook material located on the patient facing side 12b of the engagement members 26 and 28. A midpoint of the length of the belt 14 preferably includes a handle 36 to identify the midpoint and to facilitate adjustment of the length of the brace 10 as described more fully below.

The brace 10 is assembled by passing the belt 14 through the slits 22a and 24a to span the belt across the channel 20 on the outer side 12a of the plate 12. Initially, the belt 14 is oriented so that the handle 36 is aligned with the middle of the channel 20, which provides the brace 10 at a maximum length. As will be noted, the loop material 34 is engaged by the hook material located on the patient facing side 12b of the engagement members 26 and 28, which are in their closed positions so as to be flat with the planar portions 22 and 24. In this orientation, the brace 10 is maintained at the maximum length.

Additional securement of the belt 14, and hence the brace 10, at a desired length is provided by a hinged cover 40. The cover 40 is desirably made of a soft fabric material, but may be of other construction. The cover 40 is hingedly coupled to the plate 12 and folds over the portions of the belt 14 located in the channel 20. The cover 40 may include hook material to also cooperate with the loop material 34 of the belt 14, and maintain the cover 40 closed against the belt 14 and in releasable frictional engagement therewith. In this regard, it will be understood that the indicated hook and loop materials may be reversed, and that other cooperating fastener devices may be utilized.

Figure 7:
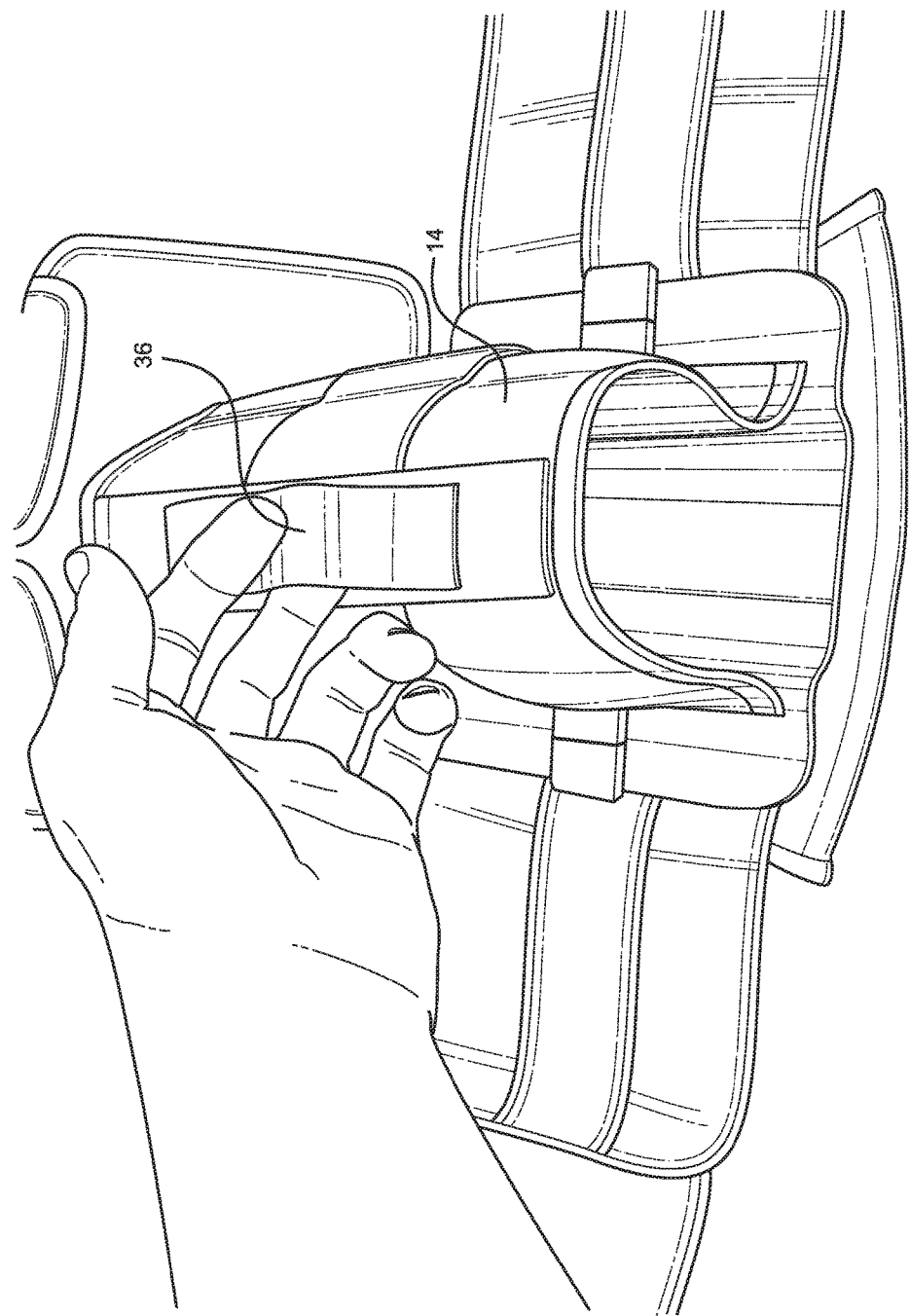
FIG. 7 shows adjustment of the brace of FIG. 5 to a smaller size setting.

To shorten the effective length of the belt 14, and hence of the brace 10, the cover 40 is lifted and the engagement members 26 and 28 are hingedly pivoted to their open positions. This disengages the hook and loop engagement of the belt 14 therefrom. The handle 36 of the belt 14 is then grasped and pulled upwardly, such as shown in FIG. 7.

Figure 8:
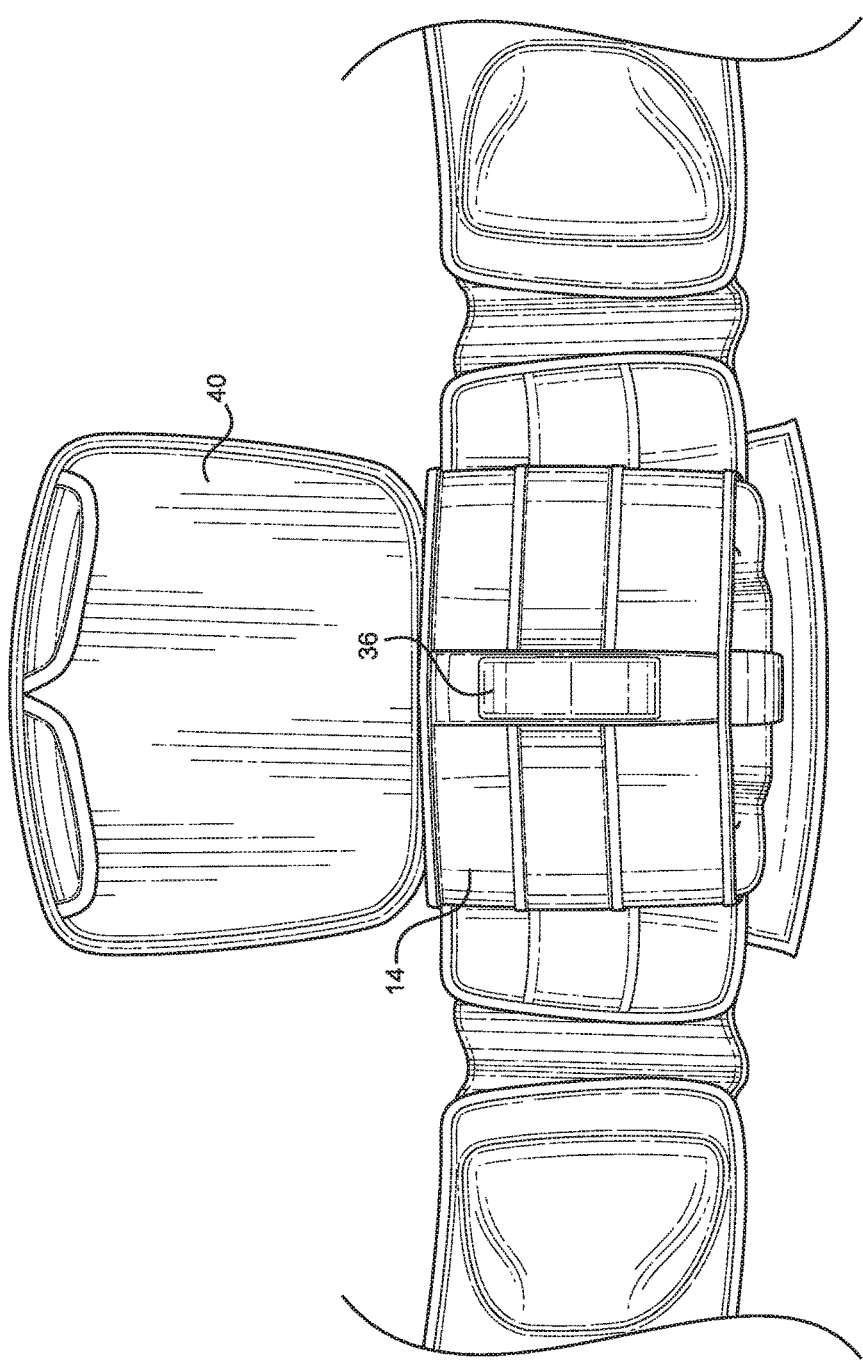
FIG. 8 shows the brace at the smaller size setting.

As will be appreciated, this uniformly reduces the length from each end of the belt 14 and accumulates excess portions of the belt 14 adjacent the channel 20. The engagement members 26 and 28 are then closed to maintain the effective belt length. The excess belt material may be folded or the like as shown in FIG. 8 to neatly store the excess material in the channel 22, and the cover 40 closed to overlie the excess material and otherwise secure the brace 10 at the adjusted length. This procedure may be repeated or reversed as desired to adjust the length of the brace 10 to be incrementally longer or shorter.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

The invention claimed is:

1. An adjustable length spinal brace, comprising:
an elongate belt; and
a belt adjustment plate having an outer side and an opposite patient faceable side configured to be positionable adjacent a spine or back portion of a patient, the belt adjustment plate having spaced apart belt passage slits through which the belt is received and belt engagement members that are pivotally adjustable relative to the plate to engage or disengage the belt,
wherein the belt engagement members are engaged with the belt to maintain a desired length of the brace, and are disengaged from the belt to permit adjustment of the length of the brace to either lengthen or shorten the length of the brace,
wherein the belt adjustment plate includes a curved central channel portion flanked on either side by planar portions, with the belt passage slits located on the planar portions adjacent the channel portion, and the belt engagement members are located adjacent lateral edges of the planar portions.

2. The brace of claim 1, wherein a midpoint of the belt includes a handle.

3. The brace of claim 2, wherein the handle is aligned with a middle of the curved central channel portion when the brace is at maximum length.

4. The brace of claim 1, wherein the planar portions include open spaces, and the belt engagement members comprise doors that pivot to open towards the outer side of the plate.

5. An adjustable length spinal brace, comprising:
an elongate belt; and
a belt adjustment plate having an outer side and an opposite patient faceable side configured to be positionable adjacent a spine or back portion of a patient, the belt adjustment plate having spaced apart belt passage slits extending through the opposite sides of the plate and through which the belt is received and belt engagement members that are pivotally adjustable relative to the plate to engage or disengage the belt,
wherein the belt engagement members are engaged with the belt to maintain a desired length of the brace, and are disengaged from the belt to permit adjustment of the length of the brace to either lengthen or shorten the length of the brace.

* * * * *